(12) United States Patent
Takao et al.

(10) Patent No.: US 7,921,696 B2
(45) Date of Patent: Apr. 12, 2011

(54) LIQUID CHROMATOGRAPH DEVICE

(75) Inventors: Kunihiko Takao, Tsuchiura (JP);
Hironori Kaji, Hitachinaka (JP);
Masahito Ito, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 126 days.

(21) Appl. No.: 12/037,111

(22) Filed: Feb. 26, 2008

(65) Prior Publication Data

US 2008/0296209 A1    Dec. 4, 2008

Related U.S. Application Data

(63) Continuation of application No. 11/171,216, filed on Jul. 1, 2005, now Pat. No. 7,350,401, and a continuation-in-part of application No. 10/695,992, filed on Oct. 30, 2003, now Pat. No. 7,588,423.

(30) Foreign Application Priority Data

Jul. 1, 2004 (JP) .................................. 2004-195940

(51) Int. Cl.
*G01N 30/00* (2006.01)
*B01D 15/08* (2006.01)
(52) U.S. Cl. ........................................ 73/61.52; 210/101
(58) Field of Classification Search .................. 73/53.01, 73/61.52; 210/198.2, 191, 101
See application file for complete search history.

(56) References Cited

U.S. PATENT DOCUMENTS

| | | | |
|---|---|---|---|
| 4,681,513 A | 7/1987 | Saito et al. | |
| 5,795,469 A | 8/1998 | Quinn | |
| 5,852,231 A | 12/1998 | Kaji | |
| 5,968,367 A | 10/1999 | Quinn | |
| 6,129,840 A * | 10/2000 | Kitaoka | 210/198.2 |
| 6,923,916 B1 * | 8/2005 | Hiraku et al. | 210/656 |
| 7,063,785 B2 | 6/2006 | Hiraku et al. | |
| 7,588,423 B2 * | 9/2009 | Takao et al. | 417/254 |
| 2004/0164013 A1 | 8/2004 | Takao et al. | |
| 2004/0178133 A1 | 9/2004 | Deguchi et al. | |
| 2005/0023205 A1 | 2/2005 | Hiraku et al. | |
| 2005/0061722 A1 | 3/2005 | Takao et al. | |
| 2005/0084386 A1 | 4/2005 | Mori et al. | |
| 2005/0095145 A1 | 5/2005 | Hiraku et al. | |

FOREIGN PATENT DOCUMENTS

| | | |
|---|---|---|
| JP | 63-75375 | 4/1988 |
| JP | 2003-107065 A | 9/2003 |
| JP | 2004-137974 | 5/2004 |

OTHER PUBLICATIONS

Japanese Office Action of Japanese Appl. No. 2004-195940 dated May 19, 2009.
Japanese Office Action of Japanese Appl. No. 2006-270299 dated May 26, 2009.

* cited by examiner

*Primary Examiner* — Hezron Williams
*Assistant Examiner* — Rodney T Frank
(74) *Attorney, Agent, or Firm* — Antonelli, Terry, Stout & Kraus, LLP.

(57) ABSTRACT

This liquid feeding system has the first and second pumps each of which is provided with a plunger. Liquid sucked through each of the pump suction ports is discharged out of the discharging port through the first pump and/or second pump. Under the starting operation mode, the second pump is stopped and only the first pump is operated. When the discharging pressure at the discharging port reaches up to a predetermined value, the starting operation mode is changed over to the normal operation mode. Under the normal operation mode, the first pump is stopped and only the second pump is operated.

11 Claims, 12 Drawing Sheets

# LIQUID CHROMATOGRAPH DEVICE

CROSS-REFERENCE TO RELATED APPLICATION

This application is a continuation application of U.S. application Ser. No. 11/171,216, filed Jul. 1, 2005, now U.S. Pat. No. 7,350,401 the contents of which are incorporated herein by reference.

This application is also a continuation-in-part of U.S. application Ser. No. 10/695,992, filed Oct. 30, 2003, now U.S. Pat. No. 7,588,423.

The present application claims priority from Japanese Application JP2004-195940 filed on Jul. 1, 2004, the content of which is hereby incorporated by reference into this application.

BACKGROUND OF THE INVENTION

This invention relates to a liquid feeding system suitable for feeding liquid at low flow rate and more particularly to a liquid feeding system which is preferable in its application to a liquid chromatograph.

As a pump for liquid chromatograph, there has been known in the art to provide a plunger pump having two plungers. In such a plunger pump as above, the two plungers are independently driven with a motor and a pulsation of flow rate is reduced through a cooperative driving of both plungers.

Example described in the gazette of Japanese Patent Laid-Open No. 75375/1988 shows that a second plunger once performs a reciprocating operation while a first plunger performs a reciprocating operation and then a pulsation in flow rate generated through a sucking operation of the first plunger is corrected through operation of the second plunger. That is, the first plunger determines a liquid feeding flow rate and the second plunger is used for correcting a pulsation of the first plunger.

Normally, when the pump for a liquid chromatograph is operated, at first, eluate is filled in the pump and a piping to discharge air bubbles. Upon completion of a preparation work performed in this way, subsequently, the pump is activated and the operation is changed over to its normal operation when a discharging pressure reaches a predetermined target value. Upon starting the normal operation, a measurement by the liquid chromatograph is started.

The pump for liquid chromatograph requires a liquid feeding of low flow rate. For example, it is required to perform a liquid feeding of quite low flow rate under a level of micro-litter (µl) and nano-litter (nl) per minute is required. Either such a pump of low flow rate or a pump of quite low flow rate requires a longer hour after starting a preparation work and by starting of a normal operation. In other words, a starting time at the time of pump energization is extended.

BRIEF SUMMARY OF THE INVENTION

It is an object of the present invention to reduce a starting time at the time of energization of the pump.

In order to accomplish the object above, the liquid feeding system of the present invention has the first and second pumps each provided with a plunger. Liquid sucked through the suction port is discharged out of a discharging port through the first and second pumps. Under a starting operation mode, the second pump is stopped and only the first pump is operated. When the discharging pressure at the discharging port reaches a predetermined value, the starting operation mode is changed over to the normal operation mode. Under the normal operation mode, the first pump is stopped and only the second pump is operated. In accordance with the present invention, it is possible to reduce the starting time at the time of starting the pump.

BRIEF DESCRIPTION OF THE SEVERAL VIEWS OF THE DRAWING

FIGS. 1 to 4 are views for illustrating one preferred embodiment of the liquid feeding system of the present invention, wherein FIGS. 1 and 2 show a block diagram.

FIGS. 3 and 4 are views for illustrating a method for driving an active valve.

DETAILED DESCRIPTION OF THE INVENTION

Figure 1:
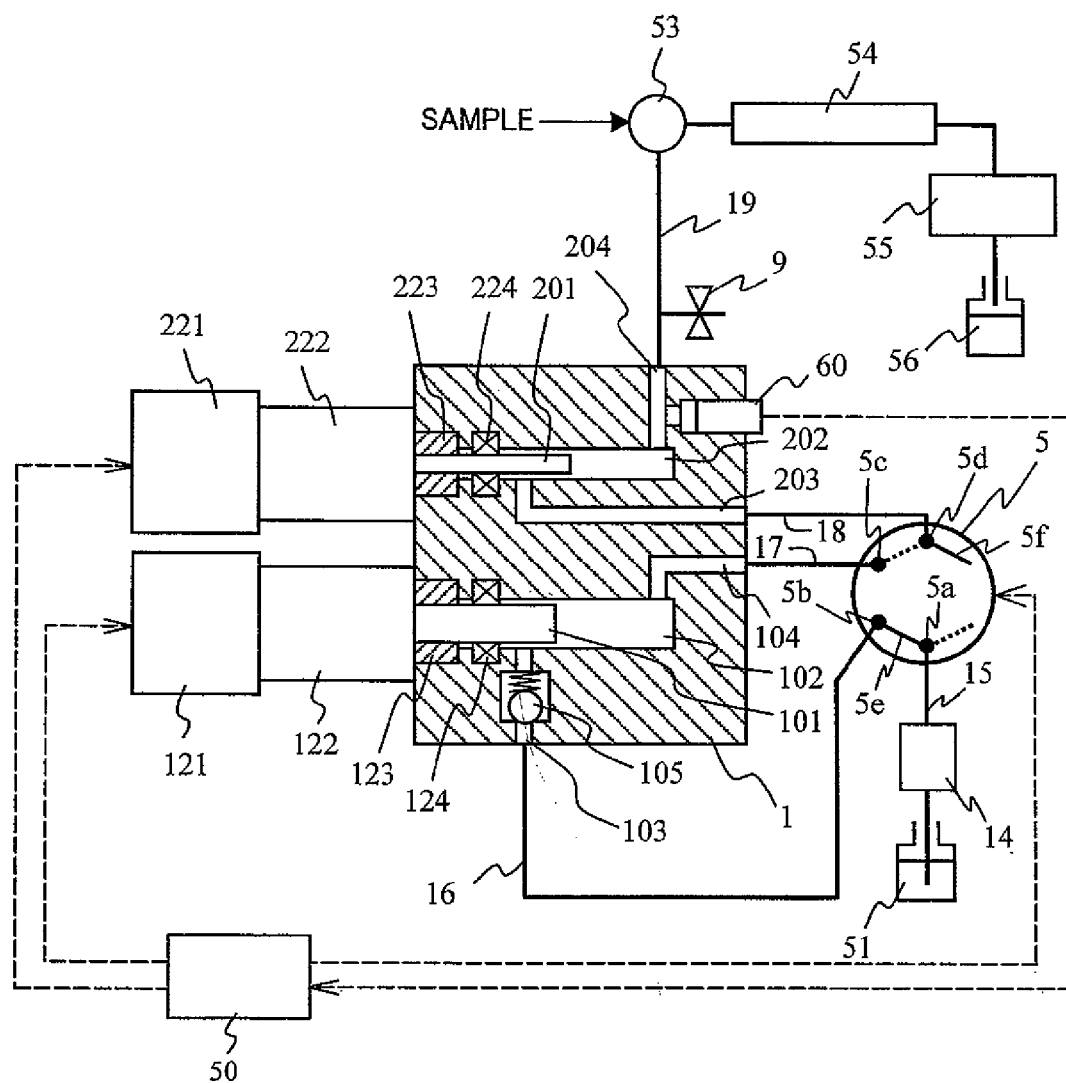

Referring now to the drawings, one preferred embodiment of the present invention will be described as follows.

Figure 2:
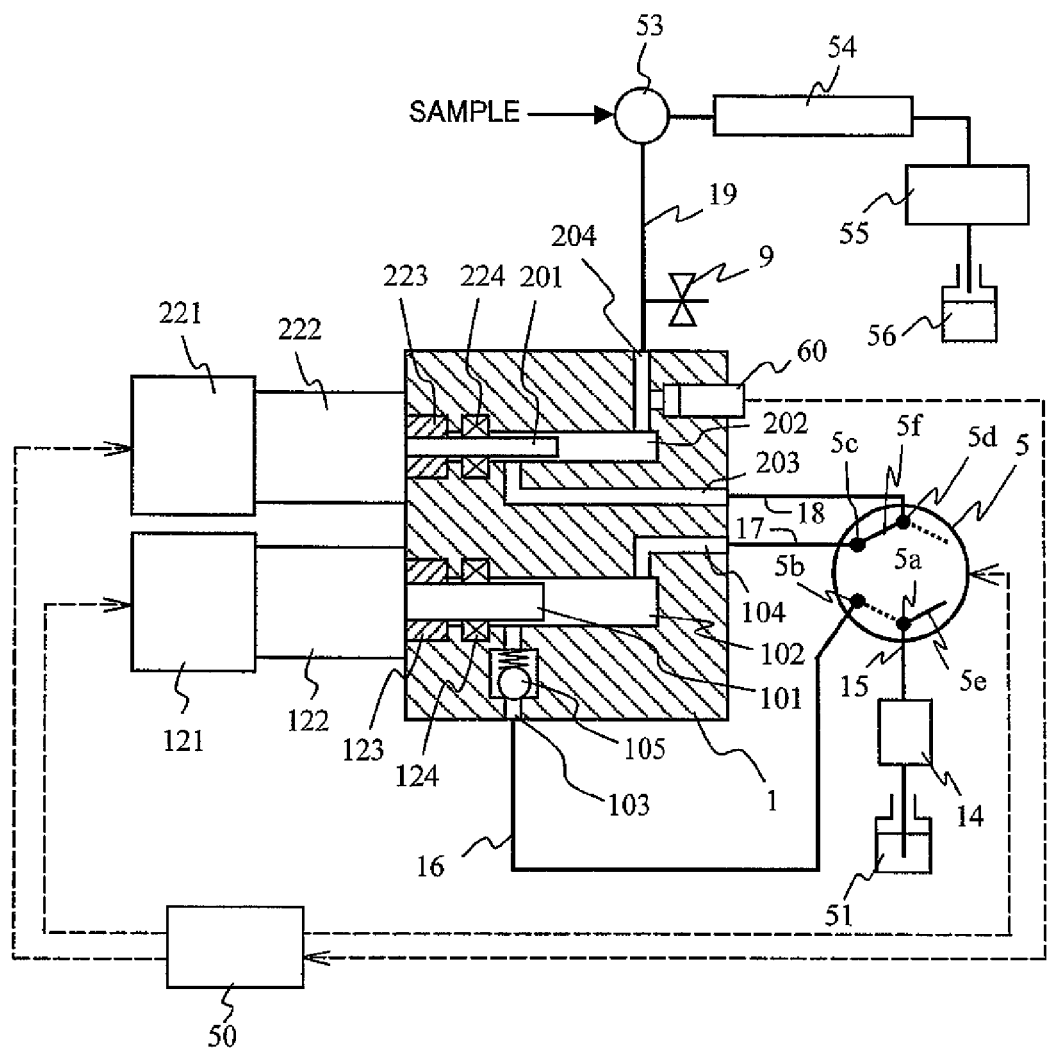

FIGS. 1 and 2 illustrate a liquid chromatograph device using the liquid feeding system in accordance with the present invention. The liquid chromatograph device comprises a liquid feeding system, an injector 53, a column 54, a detector 55 and a storing tank 56. The liquid feeding system of the present invention feeds a quite low flow rate of 0.1 mL (nano litter)/min to 50 µL (micron litter)/min, for example, to the column 54.

The liquid feeding system of the present preferred embodiment comprises a storing tank 51 for storing eluate or solvent, a deaeration device (degassing unit) 14, an active valve 5 having four ports, a plunger pump device 1 having two plungers, linear motion mechanisms (actuators) 122, 222 connected to the plunger, motors 121, 221 for driving the linear motion mechanisms and a controller 50 for controlling the motors 121, 221 and the active valve 5. The active valve 5 is connected to the storing tank 51 through the deaeration device 14 and the suction pipe 15.

The plunger pump device 1 is connected to the active valve 5 through the suction pipe 16, an intermediate discharging pipe 17 and an intermediate suction pipe 18, and is further connected to the injector 53 through the discharging pipe 19. The discharging pipe 19 is provided with a drain valve 9.

The plunger pump device 1 has a first pressurizing chamber 102 and a second pressurizing chamber 202 and these pressurizing chambers are liquid sealed with seals 124, 224. Each of the first plunger 101 and the second plunger 201 is arranged at each of the first pressurizing chamber 102 and the second pressurizing chamber 202. The first plunger 101 and the second plunger 201 are slidably held by bearings 123, 223.

Both a suction passage 103 and the discharging passage 104 are connected to the first pressurizing chamber 102. The suction passage 103 is connected to the suction pipe 16. A suction check valve 105 is arranged at the suction passage 103. The discharging passage 104 is connected to the intermediate discharging pipe 17. The suction passage 203 and the discharging passage 204 are connected to the second pressurizing chamber 202. The discharging passage 204 is connected to the discharging pipe 18. The discharging passage 204 is connected to the discharging pipe 19. The discharging passage 204 is provided with a pressure sensor 60. Further, a pressure in the discharging passage 204 detected by the pressure sensor 60 is defined herein as a pump discharging pressure.

A segment including the first pressurizing chamber 102, first plunger 101, motor 121 for driving the plunger and a linear motion mechanism 122 is defined as a first pump; and another segment including the second pressurizing chamber 202, second plunger 201, motor 221 for driving the plunger and a linear motion mechanism 222 is defined herein as a second pump. As shown in the drawings, a diameter of the first plunger 101 is larger than a diameter of the second plunger 201 and accordingly, a flow rate of the first pump is larger than a flow rate of the second pump.

The active valve 5 is a rotary valve for changing-over a flow passage by an external driving part (not shown) and it has four ports 5a, 5b, 5c and 5d and two flow passages 5e, 5f. Volume of each of the flow passages 5e, 5f is quite small. The first port 5a is connected to the suction pipe 15, the second port 5b is connected to the suction pipe 16, the third port 5c is connected to the intermediate discharging pipe 17 and the fourth port 5d is connected to the intermediate suction pipe 18.

FIG. 1 shows a state in which the first port 5a and the second port 5b are connected by the flow passage 5e, although the third port 5c and the fourth port 5d are not connected to each other. FIG. 2 shows a state in which the third port 5c and the fourth port 5d are connected by the flow passage 5c, although the first port 5a and the second port 5b are not connected to each other.

Rotation of each of the motors 121, 221 is converted into a linear motion by the linear motion mechanisms 122, 222 so as to cause each of the first plunger 101 and the second plunger 201 to be reciprocated. The controller 50 gives a driving signal to the motors 121, 221 in response to a signal of the pressure sensor 60 and at the same time gives a valve opening or closing signal to the active valve 5.

Schematic liquid feeding routes at the liquid feeding system in the present preferred embodiment will be described. At first, as shown in FIG. 1, when the first port 5a and the second port 5b are connected by the flow passage 5e, solution in the storing tank 51 is guided to the first port 5a of the active valve 5 through the deaeration device 14 and the suction pipe 15 and then the solution is guided to the suction passage 103 of the plunger pump device 1 through the first flow passage 5e, the second port 5b and the suction pipe 16. The solution is guided to the first pressurizing chamber 102 through the suction check valve 105.

In turn, when the third port 5c and the fourth port 5d are connected by the second flow passage 5f as shown in FIG. 2, the solution in the first pressurizing chamber 102 is guided to the third port 5c of the active valve 5 through the discharging passage 104 and the intermediate discharging pipe 17 and then the solution is guided to the suction passage 203 of the plunger pump device 1 through the second flow passage 5f, the fourth port 5d and the intermediate suction pipe 18. Further, the solution is guided to the injector 53 through the second pressurizing chamber 202, the discharging passage 204 and the discharging pipe 19.

Sample to be analyzed is poured through the injector 53. With such an arrangement as above, the sample is mixed in the solution. The solution containing the sample is fed into the column 54 and the constituents contained in the sample are separated from each other. Each of the separated constituents is analyzed by the detector 55. Some fine silica gel particles are already filled in the column 54 and then a load pressure of about 10 MPa is generated at the plunger pump device 1 through a fluid resistance when the solution flows there. A value of the load pressure is changed in response to a diameter of the column and its passing flow rate.

Figure 3:
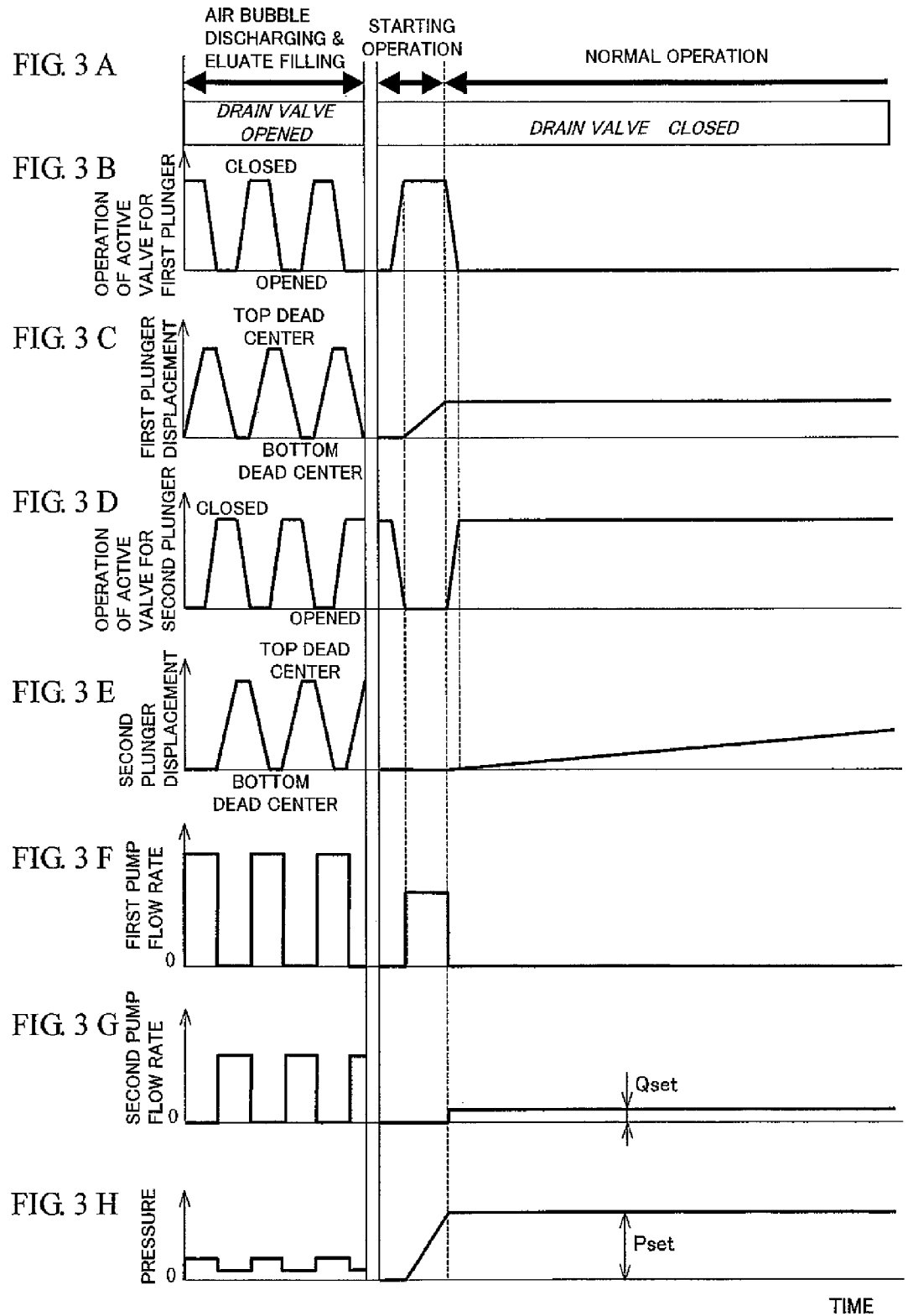

Referring to FIG. 3, an operation of the liquid feeding system of the present preferred embodiment will be described. Concurrently, FIGS. 1 and 2 are also referred to. FIG. 3A shows a drain valve opening or closing operation, FIG. 3B shows an opening or closing operation of the active valve 5 in respect to the first plunger 101, FIG. 3C shows a displacement of the first plunger 101, FIG. 3D shows an opening or closing operation of the active valve 5 in respect to the second plunger 201, FIG. 3E shows a displacement of the second plunger 201, FIG. 3F shows a first pump flow rate, FIG. 3G shows a second pump flow rate and FIG. 3H shows a discharging pressure of the pump detected by the pressure sensor 60. An X-axis denotes a time.

In addition, as shown in the sample of FIG. 1, a state in the active valve 5 in which the first port 5a and the second port 5b are connected by the flow passage 5e and the third port 5c and the fourth port 5d are not connected is defined as "opened" in respect to the first plunger 101 and is also defined as "closed" in respect to the second plunger 201. At this time, the first pressurizing chamber 102 is connected to the solution in the storing tank 51 via the active valve 5, but is not connected to the second pressurizing chamber 202.

As shown in FIG. 2, the state that the third port 5c and the fourth port 5d are connected by means of the flow passage 5f, and the first port 5a and the second port 5b are not connected thereby, is defined as "closed" for the first plunger 101, and is defined as "opened" for the second plunger 201. Then, the first pressurizing chamber 102 is connected to the second pressurizing chamber 202 via the active valve 5; but is not connected to the solution in the storing tank 51. When the active valve 5 is opened to the first plunger 101, it is closed to the second plunger 201. Inversely, when the valve is closed to the first plunger 101, it is opened to the second plunger 201.

Further, the first plunger 101 and the second plunger 201 are defined such that a state in which they are pulled in by the motors 121, 221 and the linear motion mechanisms 122, 222, i.e. they are arranged at the left end of the pressurizing chamber in FIGS. 1 and 2 is defined as being set at a bottom dead center and in turn a state in which they are pushed in by the motor 21 and the linear motion mechanism 22, i.e. they are arranged at the right end of the pressurizing chamber in FIGS. 1 and 2 is defined as being set at a top dead center.

Under the eluate filling and air bubble discharging mode before starting test in the preferred embodiment, the first pump and the second pump are used, and under the starting operation mode, the first pump is used and when a quite low flow rate liquid feeding under the normal operation mode is to be carried out, the second pump is used.

At first, the air bubble discharging and eluate filling mode will be described. Under the air bubble discharging and eluate filling mode, the air bubbles in the pump, passage and pipe contained in the liquid feeding system of the preferred embodiment are discharged out and then the eluate is filled. As shown in FIG. 3A, the drain valve 9 is released. Comparing FIGS. 3B and 3D to each other shows that an opening or closing operation of the active valve 5 for the second plunger 201 is delayed by a semi-period relative to the opening or closing operation for the first plunger.

Comparing FIGS. 3C and 3E to each other shows that when the first pump is in the suction stroke, the second pump is in the discharging stroke. Inversely, when the first pump is in the discharging stroke, the second pump is in the suction stroke.

Comparing FIGS. 3B through 3E shows that a reciprocating motion of the second plunger 201 is delayed by a semi-period relative to the reciprocating motion of the first plunger 101. When the first plunger 101 is moved from its drawn top dead center to its bottom dead center, the second plunger 201 is pushed in and moved from the bottom dead center to the top dead center. That is, the suction stroke at the first pump becomes a discharging stroke at the second pump. In turn, when the first plunger 101 is pushed in and moved from the bottom dead center to the top dead center, the second plunger 201 is drawn into and moved from the top dead center to the bottom dead center. That is, the discharging stroke at the first pump becomes the suction stroke at the second pump.

Comparing FIGS. 3F and 3G to each other shows that operations of the first plunger and the second plunger 2 are delayed in period by ¼ in respect to the opening or closing operation of the active valve 5. Accordingly, each of the opening or closing operation of the active valve 5 in FIG. 3B in respect to the first plunger 101, the reciprocating motion of the first plunger 101 in FIG. 3C, the opening or closing operation of the active valve 5 in respect to the second plunger 2 in FIG. 3D and the reciprocating motion of the second plunger 2 in FIG. 3E is delayed in sequence in a period by ¼, respectively.

For example, as shown in FIG. 3B, the active valve 5 is changed from the "closed" state to the "opened" state in respect to the first plunger 101. Next, as shown in FIG. 3C, the first plunger 101 is changed from the top dead center to the bottom dead center with a delay of period by ¼ to perform the suction stroke of the first pump. Next, as shown in FIG. 3D, the active valve 5 is changed from the "closed" state to the "opened" state in respect to the second plunger 2 with a delay of period by ¼. Next, as shown in FIG. 3E, the second plunger 2 is changed from the top dead center to the bottom dead center with a delay of period by ¼ to perform the suction stroke of the second pump.

As shown in FIG. 3B, the active valve 5 is changed from the "opened" state to the "closed" state in respect to the first plunger 101 with a delay of half-period. Then, as shown in FIG. 3C, the first plunger 101 is changed from the bottom dead center to the top dead center with a delay of period by ¼ to perform the discharging stroke of the first pump. Next, as shown in FIG. 3D, the active valve 5 is changed from the "opened" state to the "closed" state in respect to the second plunger 2 with a delay of period by ¼. Next, as shown in FIG. 3E, the second plunger 2 is changed from the bottom dead center to the top dead center with a delay of period by ¼ to perform the discharging stroke of the second pump.

As shown in FIG. 3H, although the discharging pressures of the pumps include varying components of the first pump flowing rate and the second pump flowing rate, they become substantially constant.

As shown in FIG. 3, the first plunger and the second plunger are reciprocated by several times under the air bubble discharging and eluate filling mode. A difference volume between the first pump flowing rate and the second pump flowing rate is discharged out of the drain valve 9 and simultaneously the air bubbles are also removed. In the present preferred embodiment, since the upstream side first pump has a high flowing rate, it is possible to perform an easy discharging of air bubbles accumulated in the second downstream side pressurizing chamber 202. With this operation, a test preparation can be completed in a shorter time.

Upon completion of the air bubble discharging and eluate filling mode, the first and second plungers and the active valve are arranged at their home positions described later.

Next, an operation in which the pump starting operation is transferred to the normal operation will be described as follows. The first and second plungers and the active valve are arranged at their home positions. At the home position, the active valve 5 is "opened" in respect to the first plunger 101 and "closed" in respect to the second plunger 201. In addition, the first and second plungers are arranged at the bottom dead center. Accordingly, eluate is filled in the first and second pressurizing chambers.

Subsequently, when the active valve 5 is "opened" in respect to the first plunger 101, it is merely described that the active valve 5 is "opened". Accordingly, a state in which the active valve 5 is "opened" is meant that it is "opened" in respect to the first plunger 101 and it is "closed" in respect to the second plunger 201 as shown in FIG. 1. When the active valve 5 is "closed" in respect to the first plunger 101, it is merely described that the active valve 5 is "closed". Accordingly, a state in which the active valve 5 is "closed" means that it is "closed" in respect to the first plunger 101 and it is "opened" in respect to the second plunger 201 as shown in FIG. 2.

When the active valve 5 is placed at the home position, it is "opened". At first, the drain valve 9 is closed as shown in FIG. 3A and the active valve 5 is changed from the "opened" state to the "closed" state as shown in FIG. 3B and FIG. 3D. Accordingly, as shown in FIG. 2, the first pressurizing chamber 102 is connected to the second pressurizing chamber 202 through the active valve 5. As shown in FIG. 3C, the first plunger 101 is moved from the bottom dead center toward the top dead center at a predetermined speed and the discharging stroke of the first pump is carried out. As apparent from the gradient in the graph, the moving speed of the first plunger 101 at the starting operation of the pump is slower than that of the air bubble discharging and eluate filling mode. As shown in FIG. 3E, the eluate discharged out of the first pressurizing chamber 102 is guided to the second pressurizing chamber 202 through the active valve 5 and from there, the eluate is discharged to the discharging pipe 19. At this time, the second pump is not substantially operated. Accordingly, although the flow rate of the first pump becomes a predetermined value corresponding to the moving speed of the first plunger 101, the flow rate of the second pump is zero as shown in FIG. 3G.

When the discharging pressure of the pump reaches up to the target pressure Pset as shown in FIG. 3H, the operation is changed over to the normal operation. The target pressure Pset is determined in response to a diameter of the column and a passing flow rate. When the discharging pressure of the pump reaches up to the target pressure Pset, the pressure sensor 60 informs it to the controller 50.

The controller 50 transmits a command under the normal operation mode to the first and second pumps and the active valve 5. Under the normal operation, a liquid feeding flow rate is kept constant while holding the discharging pressure to the target pressure Pset.

Under the normal operation, the active valve 5 us changed from the "closed" state to the "opened" state as shown in FIG. 3B and FIG. 3D. Accordingly, the second pressurizing chamber 202 is shut by the first pressurizing chamber 102 as shown in FIG. 1. The first plunger 101 is stopped as shown in FIG. 3C. The first plunger 101 is arranged at a predetermined position between the bottom dead center and the top dead center. Next, the second plunger 201 is moved from the bottom dead center toward the top dead center at a slow speed as shown in FIG. 3E. The discharging stroke of the second pump is executed at a slow speed. The flow rate of the first pump becomes zero as shown in FIG. 3F and a flow rate of the second pump becomes a target flow rate Qset as shown in FIG. 3G. In this example, the second plunger 201 is pushed in at a constant slow speed, thereby the discharging pressure is held at the target pressure Pset and the liquid feeding flow rate can be held at the target flow rate Qset.

When the normal operation is carried out in this way, the sample of the item to be analyzed is poured by the injector 53, the mixed solution enters into the column 54, they are separated for every constituent and then the constituents are analyzed by the detector 55.

In this example, only the first pump is operated under the pump starting operation and only the second pump is operated under the normal operation. Under this operating method, it is possible to shorten the reaching time up to the target pressure, i.e. the starting time of the pump starting time.

Next, a changing-over operation for changing-over from the starting operation to the normal operation will be described as follows. Practically, there occurs sometimes that the pump pressure shows an over-shoot from the target pressure Pset and a starting time is extended due to a reply time at the time of changing-over of the active valve 5 or a presence of the dead volume of the active valve 5. Then, its countermeasure will be described as follows.

Figure 4:
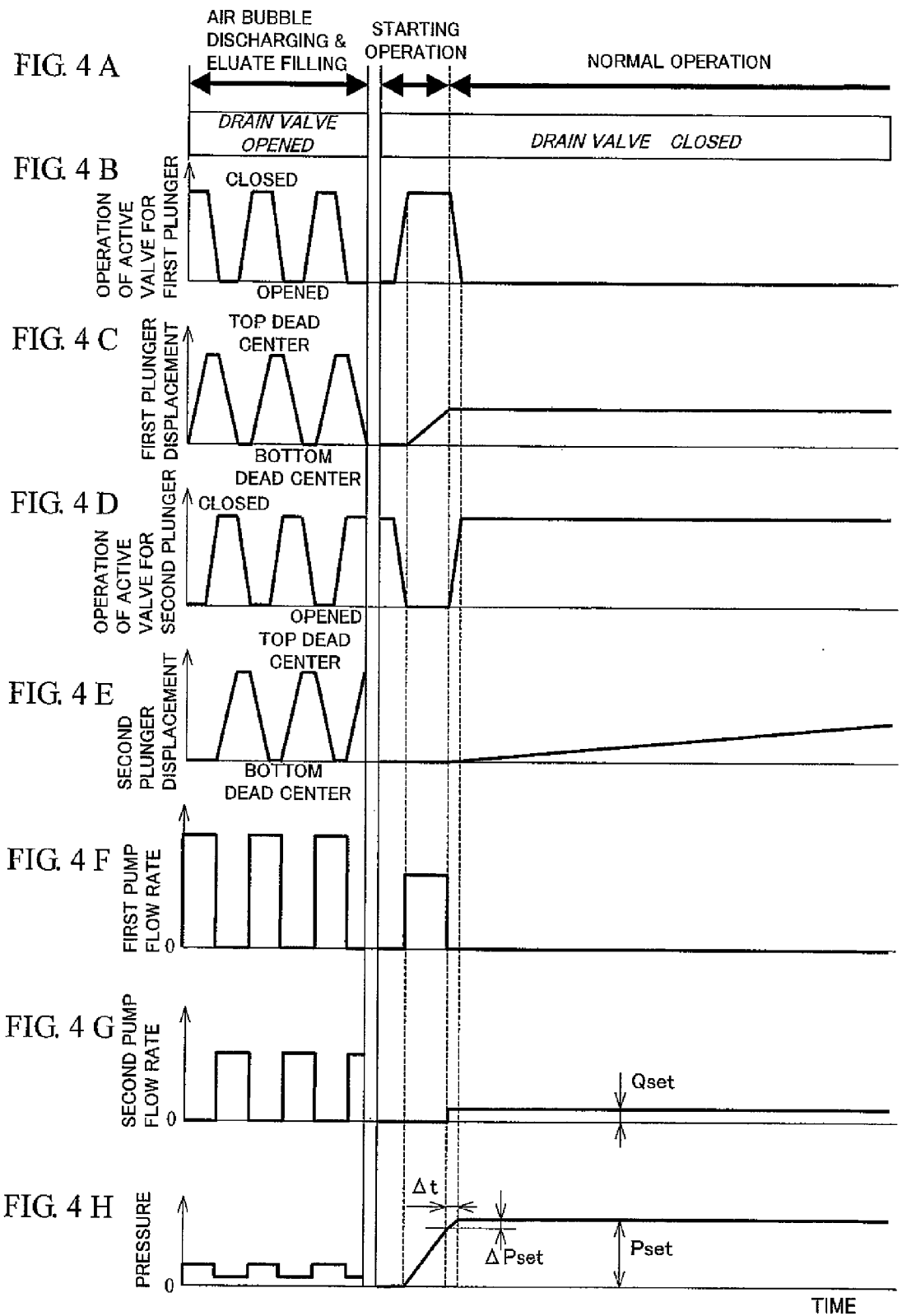

FIG. 4 illustrates another operating method for the liquid feeding system of the present invention in the same way as that shown in FIG. 3. Description of both discharging of air bubbles and filling of the eluate will be omitted because they are similar to those shown in FIG. 3.

In this example, only the first pump is operated under the starting operation of the pump in the same manner as that of the example in FIG. 3. When the pump discharging pressure reaches up to a value (Pset−ΔPset) lower only by ΔPset as shown in FIG. 4H, the operation is changed over to the normal operation. Upon starting of the normal operation, the active valve 5 is changed from its "closed" state to its "opened" state as shown in FIG. 4B and FIG. 4D. As shown in FIG. 4C, the first plunger 101 is stopped. The first pump flow rate becomes zero as shown in FIG. 4F and the second pump flow rate becomes a target flow rate Qset as shown in FIG. 4G. The pump discharging pressure is increased and reaches up to the target pressure Pset as shown in FIG. 4H.

In this example, it is possible to reduce the over-shoot from the target pressure by performing it with changing-over time from the first plunger 101 to the second plunger 201 being faster only by Δt as compared with the operating method shown in FIG. 3. Further, a gradient of the pump discharging pressure at the time Δt is smaller than a gradient of the pump discharging pressure at the starting operation.

Further, although the plunger changing-over time is adjusted for reducing the over-shoot in this example, it may also be applicable to employ another method, a method for reducing a feeding speed of the first plunger 101, for example. In this way, an operation for adjusting the plunger changing-over time or reducing the feeding speed of the first plunger 101 to reduce the over-shoot is defined as a pressure correction hereinbelow.

Then, referring to FIG. 5 and FIG. 6, an effect of the present preferred embodiment will be described.

Figure 5:
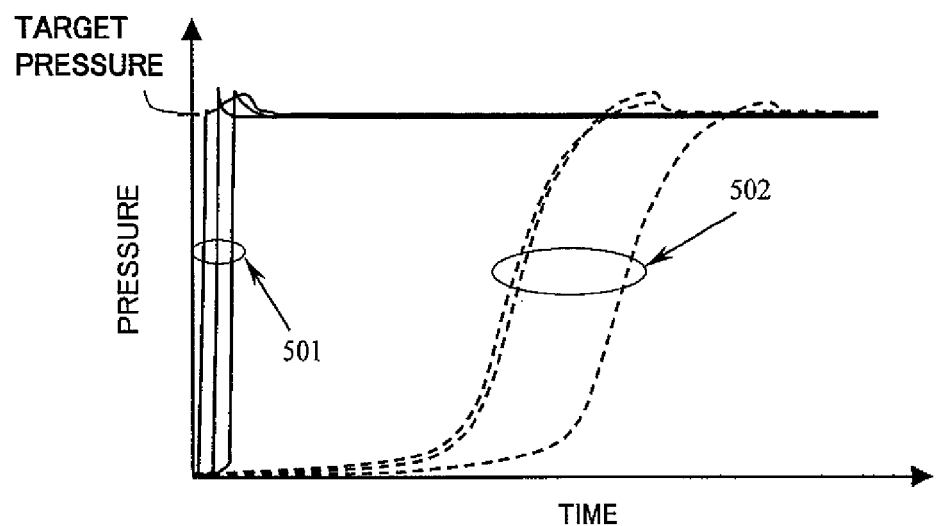
FIGS. 5 and 6 are graphs for illustrating a pressure characteristic of a pump used in a liquid feeding system in FIG. 1.

FIG. 5 shows a result of variation in the pump discharging pressure when an operation of the pump is changed from the starting operation to the normal operation. A solid line curved line 501 in FIG. 5 indicates a pump discharging pressure when the pressure correction is performed and a dotted curved line 502 indicates a pump discharging pressure when the pressure correction is not performed.

When the pressure correction is not carried out, the pump starting time is extended and at the same time a disturbance of the starting time is increased. To the contrary, when the pressure correction is carried out, the pump starting time is substantially shortened and at the same time a disturbance in the starting time is almost eliminated. Further, although not shown in the drawing, when the pressure correction is not carried out, a case when the pressure does not reach up to the target pressure in correspondence with either the target flow rate or target pressure of the second pump was generated and such a phenomenon was not generated when the pressure correction was carried out.

Figure 6:
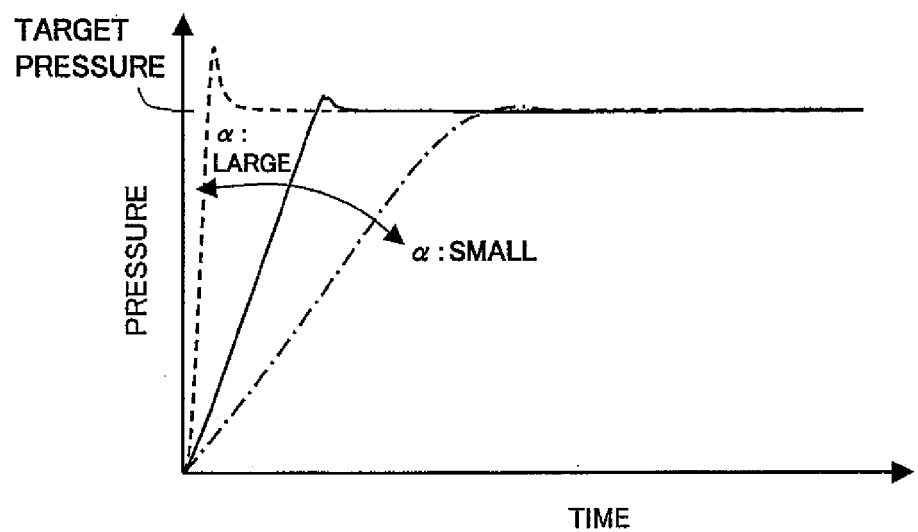

Referring to FIG. 6, when a pressure correction is carried out by the first pump (operation of the first plunger), a flow rate relation between the first pump and the second pump will be described. A following equation of $$Q1 = \alpha \cdot Q2 \qquad (\text{Ex. 1})$$

can be attained, where Q1 is a first pump set flow rate (a value in which a sectional area of the first plunger is multiplied by a feeding speed of the first plunger), Q2 is a second pump set flow rate (a value in which a sectional area of the second plunger is multiplied by a feeding speed of the first plunger) and α is a coefficient of flow rate at that time.

FIG. 6 shows a relation between the coefficient α of flow rate and a pump starting characteristic. Although the higher the coefficient α of flow rate, the shorter the pump starting characteristic, too higher coefficient value causes an over-shoot to be generated. To the contrary, although the smaller the coefficient α of flow rate, the longer a pump starting time, no over-shoot may be generated. The coefficient α of flow rate=1 corresponds to the case in which the first pump set flow rate is the same as the second pump set flow rate. When the coefficient α of flow rate=1 is applied, there may occur a case in which the pump pressure does not reach up to the target pressure. Accordingly, the coefficient α of flow rate is at least larger than 1.

As the coefficient α of flow rate, the most-suitable value is present. The most-suitable value of the coefficient α of flow rate may be different in compliance with the target pressure and the target flow rate. In other words, if the target pressure and the target flow rate are determined, the most-suitable value of the coefficient α of flow rate can be attained. When an analysis is carried out with a liquid chromatograph using the liquid feeding system of the present invention, for example, it is preferable to make a map in advance for the target pressure in respect to the target flow rate. It is also possible to perform an automatic starting-up of the liquid feeding system of this example through utilization of this map. For example, a user inputs the target pressure. The liquid feeding system reads the target flow rate corresponding to the target pressure from the map and gets the most-suitable value of the coefficient α of flow rate from the target flow rate. In this way, the most-suitable value of the coefficient α of flow rate is applied as an input value and the liquid feeding system is operated.

In the examples shown in FIG. 1 and FIG. 2, although a diameter of the first plunger is constituted to be larger than a diameter of the second plunger, it may also be applicable that the first plunger diameter and the second plunger diameter are made same to each other to cause the moving speed of the first plunger to be larger than the moving speed of the second plunger. With this arrangement above, the first pump flow rate becomes larger than the second pump flow rate.

Figure 7:
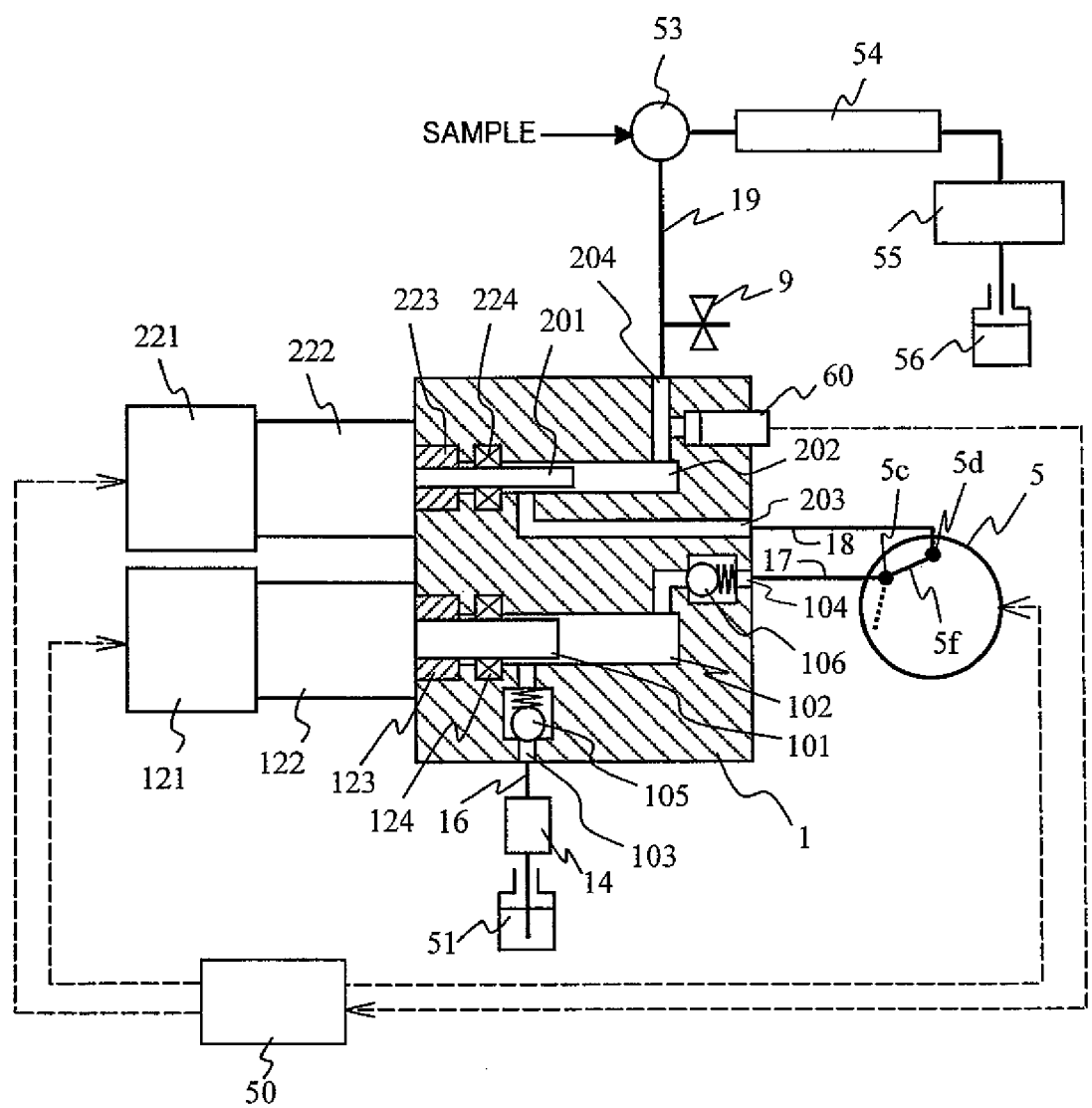
FIGS. 7 and 8 are block diagrams for showing another preferred embodiment of the liquid feeding system in accordance with the present invention.
Figure 8:
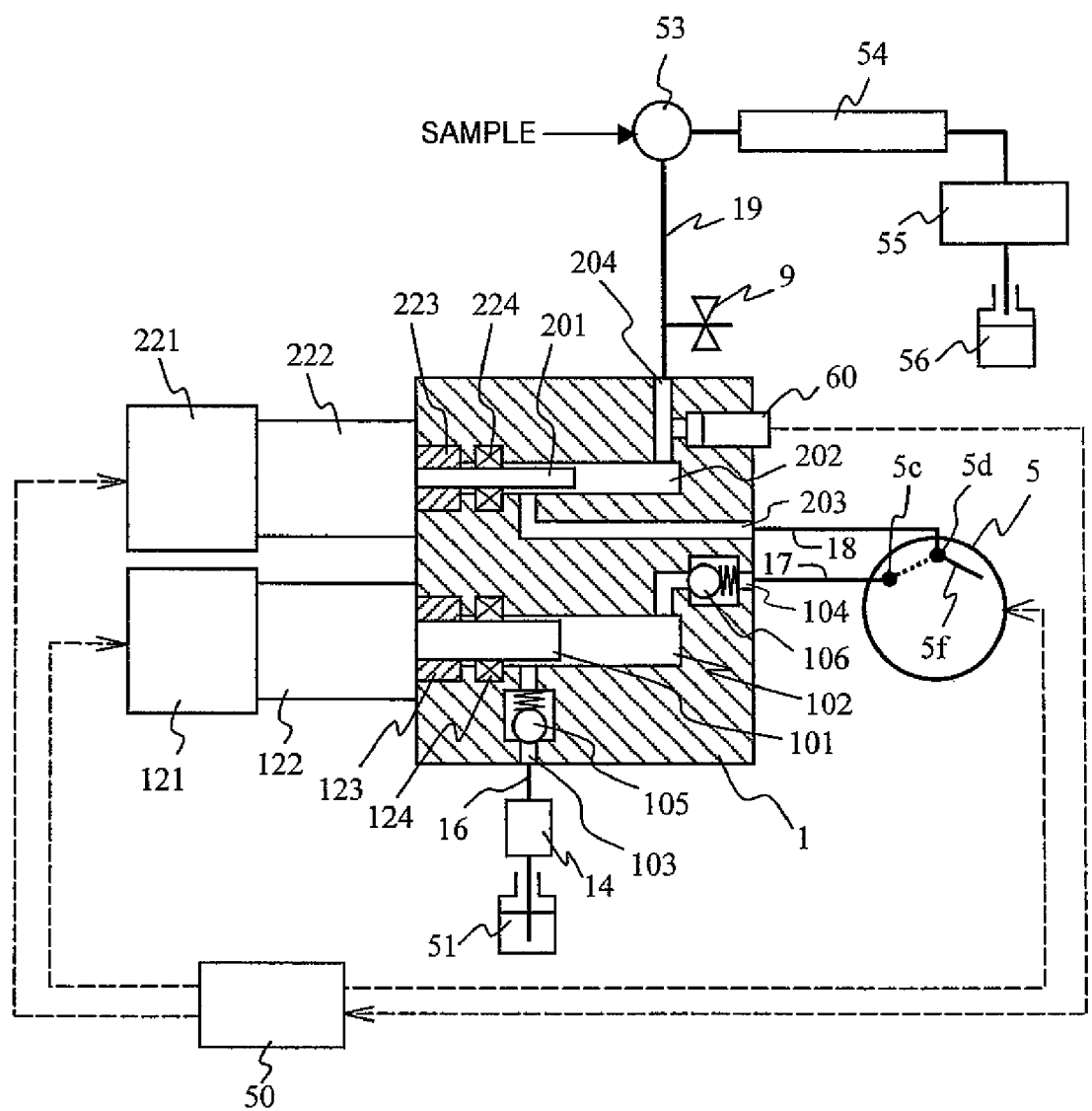
Figure 9:
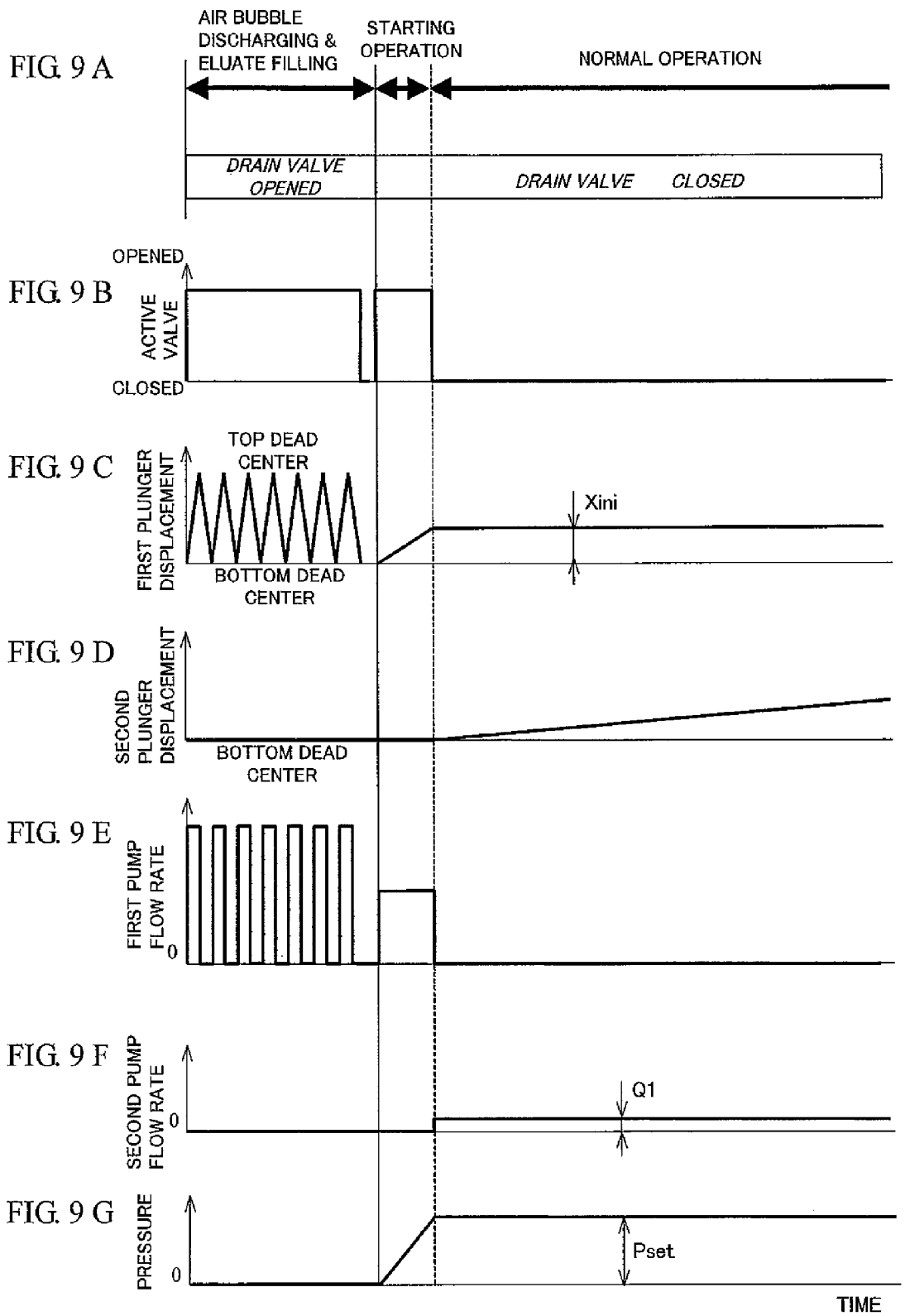
FIG. 9 is a view for illustrating a method for driving an active valve used in the system.

Referring to FIGS. 7 to 9, another example of the liquid feeding system of the present invention will be described. Same reference symbols are applied to the same portions as those of the first example in the liquid feeding system shown in FIGS. 1 to 3, and their description will be properly eliminated. In this example, the active valve 5 has two ports 5c, 5d and one flow passage 5f.

The first port 5c of the active valve 5 is connected to the discharging passage 104 of the first pump and the second port 5d is connected to the suction passage 203 of the second pump. The suction passage 103 of the first pump is connected to the storing tank 51 through a deaeration device 14 and the suction pipe 16. The discharging passage 104 of the first pump is provided with a discharging check valve 106. The first pump flow rate is larger than the second pump flow rate in the same manner as that of the first example.

FIG. 7 shows a state in which the first and second ports 5c, 5d of the active valve 5 are connected to each other by the flow passage 5f. In this case, this state is defined that the active valve 5 is "opened". FIG. 8 shows a state in which the first and second ports 5c, 5d of the active valve 5 are not connected to each other. In this case, this state is defined that the active valve 5 is "closed".

Referring to FIG. 9, a method for operating the liquid feeding system in this example will be described. At first, the air bubble discharging and eluate filling mode will be described. The drain valve 9 is "opened" as shown in FIG. 9A and the active valve 5 is "opened" as shown in FIG. 9B. The first plunger 101 is reciprocated at a fast speed as shown in FIG. 9C. At this time, the second plunger is arranged at the bottom dead center as shown in FIG. 9D. As shown in FIG. 9E, liquid is fed by an upstream side first pump having a high flow rate, the air bubbles in the first and second pumps are discharged and eluate is filled. The downstream side second pump flow rate having a small flow rate is zero. As shown in FIG. 9G, the pump discharging pressure is zero.

In this example, it is possible to perform an easy discharging of the air bubbles accumulated in the downstream side second pressurizing chamber because the air bubble discharging and eluate filling mode is carried out by the upstream side first pump having a higher capacity. With such an arrangement as above, it is possible to complete a test preparation within a shorter time. Although a flow rate of the pump is set intermittently as shown in FIG. 9E, a pulsation in flow rate under this mode does not provide any influence on a measurement precision, so that no problem occurs.

Next, changing-over in operation from the starting operation to the normal operation will be described. Under the pump starting operation, the drain valve 9 is "closed" as shown in FIG. 9A and the active valve 5 is kept at the "opened" state as shown in FIG. 9B. As shown in FIG. 9C, the first plunger 101 is moved from the bottom dead center toward the top dead center at a predetermined speed. At this time, the second plunger is arranged at the bottom dead center as shown in FIG. 9D. As shown in FIG. 9E, the first pump flow rate becomes a predetermined value in compliance with the moving speed of the first plunger 101. As shown in FIG. 9F, the second pump flow rate is zero. As shown in FIG. 9G, the pump discharging pressure is increased. When the pump discharging pressure reaches up to the target pressure Pset, the operation is changed over to the normal operation. In this example, when the position of the first plunger 101 became Xini, the pump discharging pressure reached up to the target pressure Pset.

Under the normal operation, the active valve 5 is "closed" as shown in FIG. 9B. The position of the first plunger 101 is held at Xini as shown in FIG. 9C and the second plunger 201 is pushed into the second pressurizing chamber 202 at a slow speed as shown in FIG. 9D. At this time, as shown in FIG. 9E, the first pump flow rate is zero and as shown in FIG. 9F, the second pump flow rate becomes the target flow rate Q1.

As described above, in accordance with the liquid feeding system of this example, there is provided an effect capable of performing the air bubble discharging and eluate filling within a short period of time and improving a durability of the active valve because the changing-over times of the active valve can be reduced.

Figure 10:
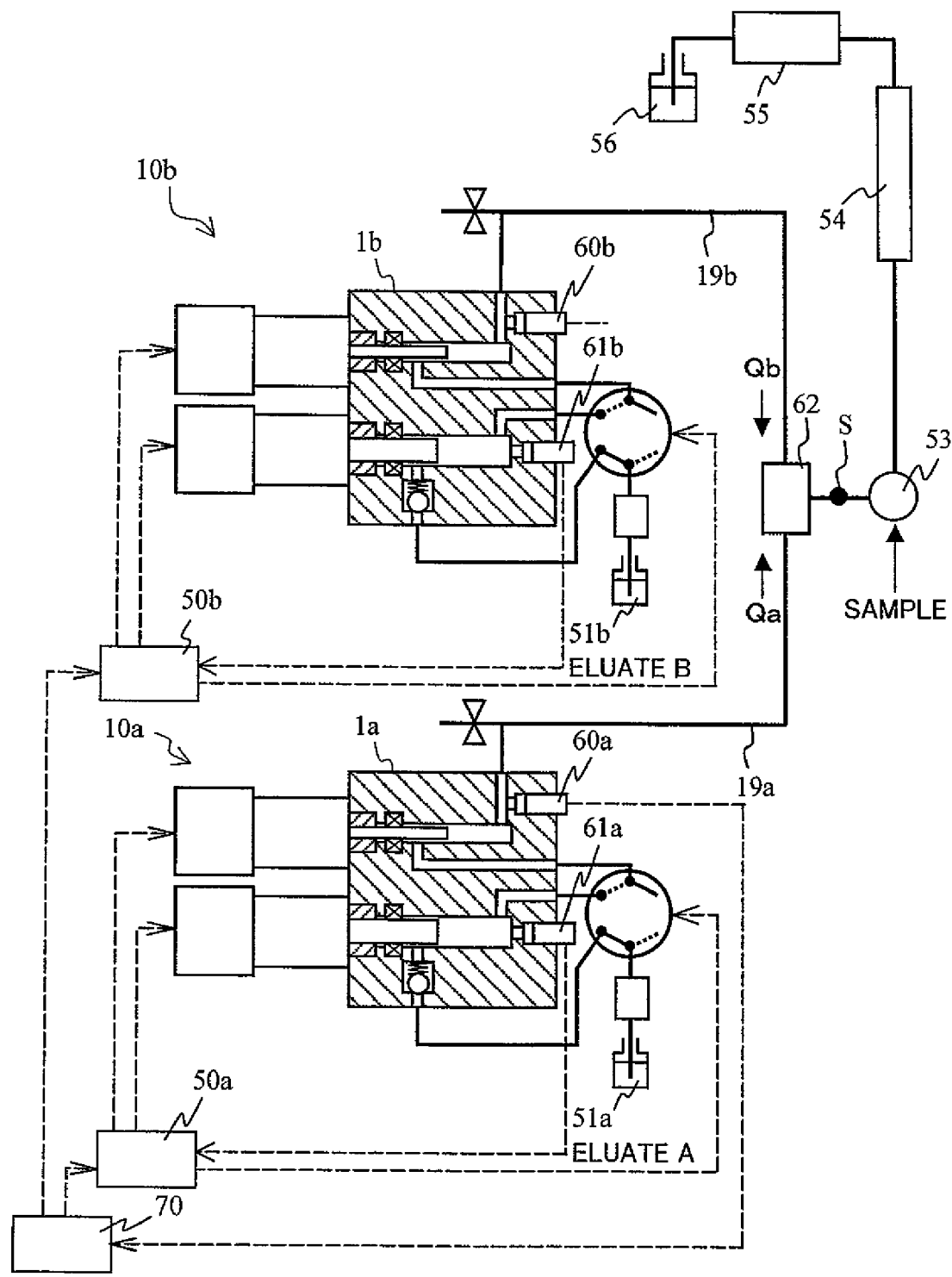
FIG. 10 is a block diagram for showing one preferred embodiment of the liquid feeding system using a high pressure gradient operating system in accordance with the present invention.

FIG. 10 shows an example of a high pressure gradient operation system. The high pressure gradient operation system has two liquid feeding systems connected to each other to perform a high pressure gradient operation. The high pressure gradient operation system of this example includes two liquid feeding systems 10a, 10b, main controller 70 and mixer 62. The second pump discharging passages in the two liquid feeding systems 10a, 10b are provided with each of the first pressure sensors 60a, 60b, and the first pressurizing chamber is provided with each of the second pressure sensors 61a, 61b. The two liquid feeding systems 10a, 10b are the same as the liquid feeding system shown in FIG. 1 except the fact that there are provided second pressure sensors 61a, 61b Each of the two liquid feeding systems 10a, 10b may be the aforesaid other liquid feeding systems in place of the liquid feeding system in FIG. 1.

Discharging pipes 19a, 19b of the two liquid feeding systems 10a, 10b are connected to the mixer 62. The discharging side of the mixer 62 is connected to the injector 53.

Figure 11:
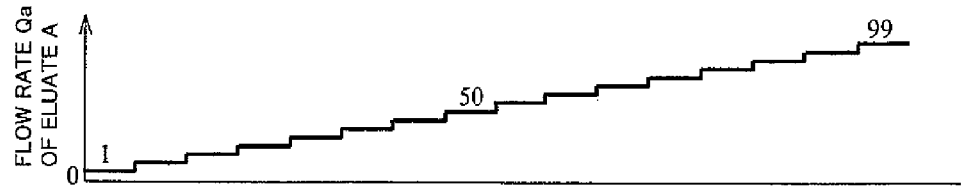
FIG. 11 is a view for illustrating its operating method.
Figure 11:
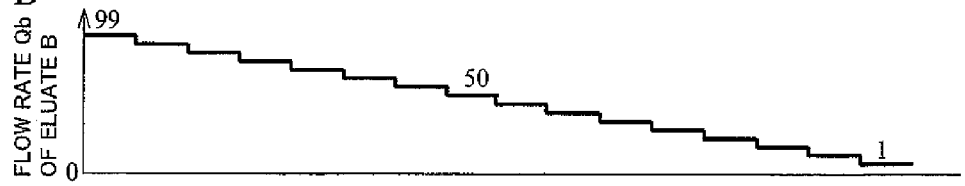
Figure 11:
Figure 11:
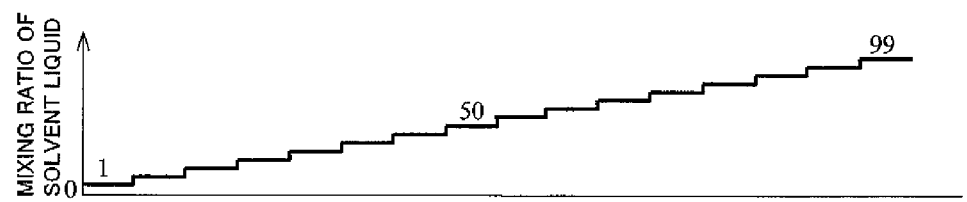
Figure 11:
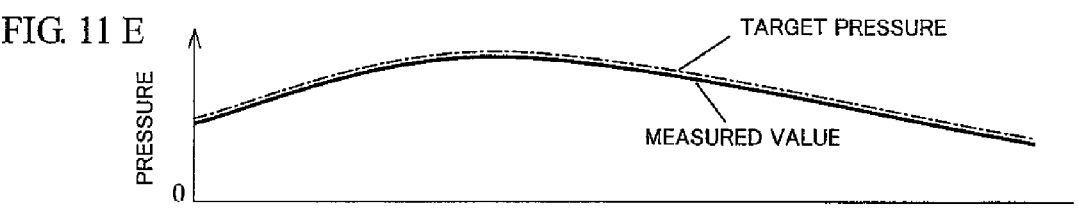
Figure 11:
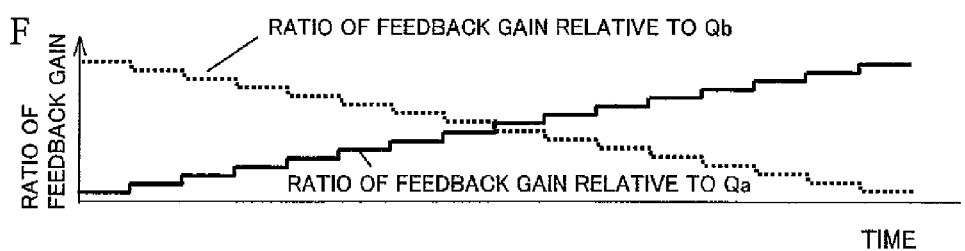

Referring to FIG. 11, the gradient operation will be described. The gradient operation is meant to feed liquid while a mixing ratio of the two kinds of eluate A and B is being changed in a stepwise manner as time passes by. That is, a ratio between the two liquid feeding flow rates Qa and Qb is changed while a total liquid feeding flow rate (Qt=Qa+Qb) is being kept constant. As shown in FIG. 11A, the flow rate Qa of the first eluate A is increased in a stepwise manner as time passes by and it is changed in a stepwise manner from Qa=1 to Qa=99, for example. As shown in FIG. 11B, a flow rate Qb of the second eluate B is decreased in a stepwise manner as time passes by, and this is changed in a stepwise manner from Qb=99 to Qb=1, for example. As shown in FIG. 11C, a total liquid feeding flow rate Qt=Qa+Qb is kept constant and its value is assumed to be 100. Further, the total liquid feeding flow rate Qt is a flow rate of the mixer 62. FIG. 11D shows a mixing ratio of solutions at the discharging point S of the mixer 62. A mixing ratio between the first eluate A and the second eluate B is increased in a stepwise manner as time passes by. It is changed in a stepwise manner from Qb/Qa=1 to Qb/Qa=99, for example. This example is a gradient in 100 steps. Accordingly, when the total liquid feeding flow rate Qt is defined as 1 µL/min, a minimum flow rate and resolution are 1/100, i.e. 10 mL/min.

FIG. 11E shows a pump discharging pressure. Two pump discharging pipes 19a, 19b are connected through the mixer 62. Ignoring either a pressure reduction or a pressure loss caused by the mixer 62 shows that the two pump discharging pressures are the same to each other. That is, the discharging pressure detected by the first pressure sensor 60a of the first pump is equal to the discharging pressure detected by the second pressure sensor 60b of the second pump. Further, the discharging pressures detected by these pressure sensors 60a, 60b are equal to the discharging pressure of the mixer 62.

As shown in FIG. 11C, even if the total liquid feeding flow rate Qt is kept constant, the pump discharging pressure is changed by about a maximum of 1.5 to 2 times as shown in FIG. 11E. This is due to the fact that when the mixing ratio between the two eluates is changed, a fluid resistance when they pass through the column is changed. When it is tried to keep the pump discharging pressure constant, in turn, the total liquid feeding flow rate Qt does not become constant.

In turn, a relation between the mixing ratio and the pressure variation is already known in reference to the past experimental data. Accordingly, a pressure variation curve when the total liquid feeding flow rate Qt is kept constant can be estimated. Thus, the discharging pressure of the mixer 62 is measured, the measured value is compared with the estimated value at the pressure variation curve and the pump may be driven with a deviation between both values being applied as a feed-back signal.

A solid curve in FIG. 11E shows measured values of the pump discharging pressure and a dotted line curve shows target pressures attained by the past experimental data.

As shown in FIG. 10, an output from the first pressure sensor 60a arranged at the pump in the first liquid feeding system is fed back to the main controller 70. The main controller 70 compares the measured value from the first pressure sensor 60a with the target pressure to attain a deviation between them. This deviation is transmitted to each of the pump controllers 50a, 50b. The controllers 50a, 50b control each of the pumps in response to the deviation.

When the pump discharging pressure is lower than the target pressure, the total liquid feeding flow rate (Qt=Qa+Qb) is reduced. Accordingly, it is satisfactory that the total liquid feeding flow rate is increased. However, it is vague which one of the two liquid feeding flow rates Qa and Qb is reduced more. When it is erroneously judged that the second liquid feeding flow rate Qb is reduced even if actually the first liquid feeding flow rate Qa is reduced and the second liquid feeding flow rate Qb is increased, a precision of the mixing ratio is deteriorated. This is a problem called as a mutual interference at the gradient operation.

In this example, it is assumed that two liquid feeding flow rates Qa and Qb are increased or decreased under the same rate. Accordingly, as shown in FIG. 11F, a feed-back gain proportional to the flow rate ratio is given in respect to the two liquid feeding flow rates Qa and Qb. That is, it performs a proportional control. When the ratio of the two liquid feeding flow rates Qa:Qb is 20:80, for example, a feed-back gain of the two liquid feeding flow rates Qa and Qb is given by (20/100)×K and (80/100)×K, respectively. K is a constant. When the total liquid feeding flow rate Qt is lack only by 5, each of the instruction values for the pump is given by 20+(20/100)×K×5 and 80+(80/100)×K×5, respectively. When K is 1, for example, the former becomes 21 and the latter becomes 84. Although applying this method cannot avoid any reduction in precision of mixing ratio due to a respective difference between the two pumps, mutual interference can be avoided.

With the foregoing arrangement, it is possible to improve a liquid feeding stability and mixing precision in the high pressure gradient system.

Figure 12:
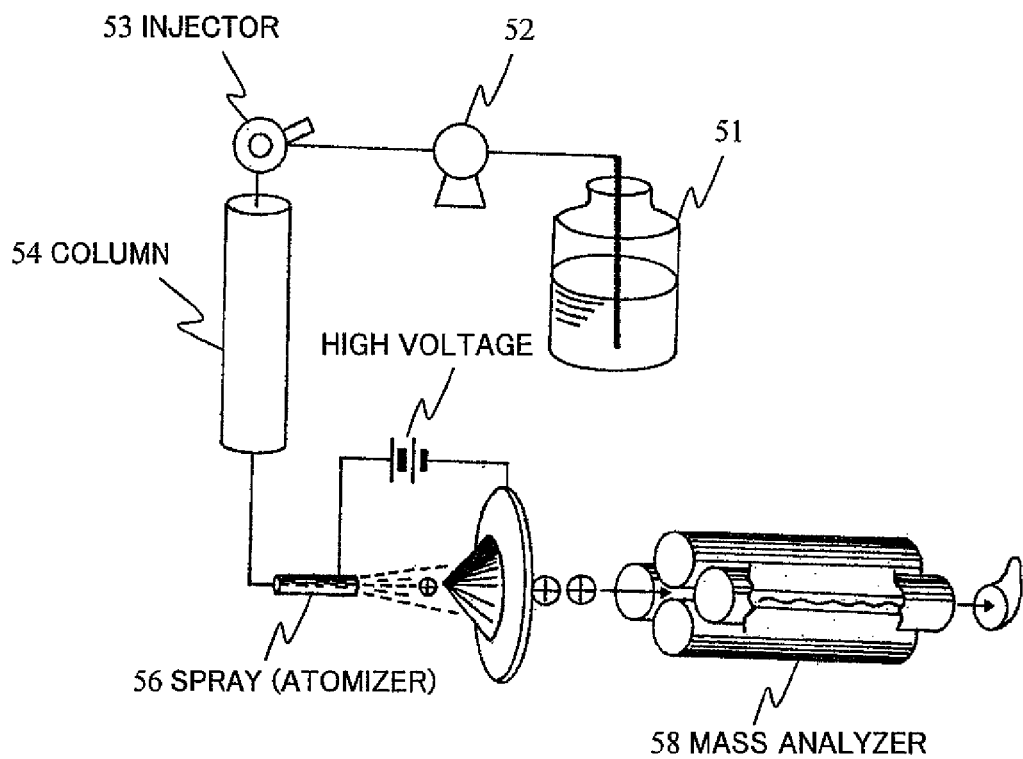
FIG. 12 is a block diagram for showing one preferred embodiment of a liquid chromatograph and a mass analyzer system using the liquid feeding system of the present invention.
Figure 12:
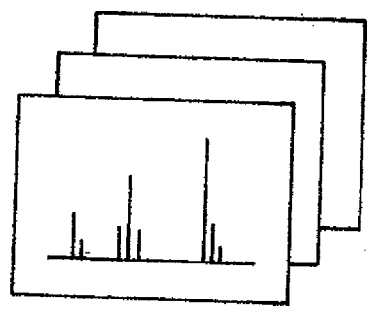
Figure 12:
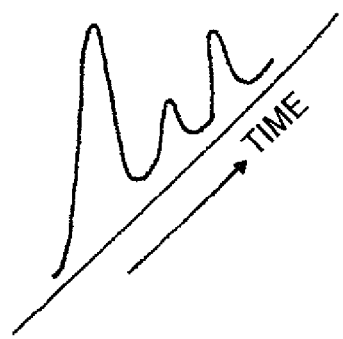

FIG. 12(a) shows an example in which a liquid chromatograph and a mass analyzing system are constituted through application of the liquid feeding system of the present invention. The liquid chromatograph includes a liquid feeding system 52, injector 53, column 54 and high voltage spray (atomizer) 56. In this example, as an interface connecting the liquid chromatograph with the mass analyzer 58, an electro-spray ionization (ESI) process used for analyzing substances having a high polarity such as protein or peptide and the like is applied. In the electro-spray ionization process, when sample solution is fed into a capillary tube applied with a high voltage of about 3 to 5 kV, quite fine spray (atomization) is generated under an atmospheric pressure and then the sample molecules are ionized. In this way, the ionized sample molecules are fed into the mass analyzer. The mass analyzer analyzes a value in which the mass is divided by an electrical charge and specifies its molecular weight.

FIG. 12(b) and FIG. 12(c) show one example of processing data at the mass analyzer. FIG. 12(b) shows a mass spectrum and FIG. 12(c) shows a mass chromatogram.

Although protein is extracted from the collected cells and analyzed in the proteome analysis, a volume of the protein contained in the cells is ultra-fine volume and its growing is also impossible. Accordingly, it is necessary to attain a low flow rate at the liquid chromatograph so as to increase a sensing precision at the liquid chromatograph and the mass analyzer system. In addition, it takes several hours as the analyzing time starting from feeding of sample to data processing.

It is possible to attain a fine amount of analytical sample fed into the liquid chromatograph by applying the liquid feeding system of the present invention to the liquid chromatograph and the mass analyzer system described above. In addition, it is possible to assure the analyzing time of longer hours because the starting time at the pump starting time is short in the liquid feeding system of the present invention. As a result, it is possible to increase the number of processing of data. In addition, when the pump pressure is monitored and reaches up to a predetermined value (the aforesaid target pressure, for example), it may also be applicable that the sample is fed and its analysis is started. With this operation, a power-saving can be accomplished.

Figure 13:
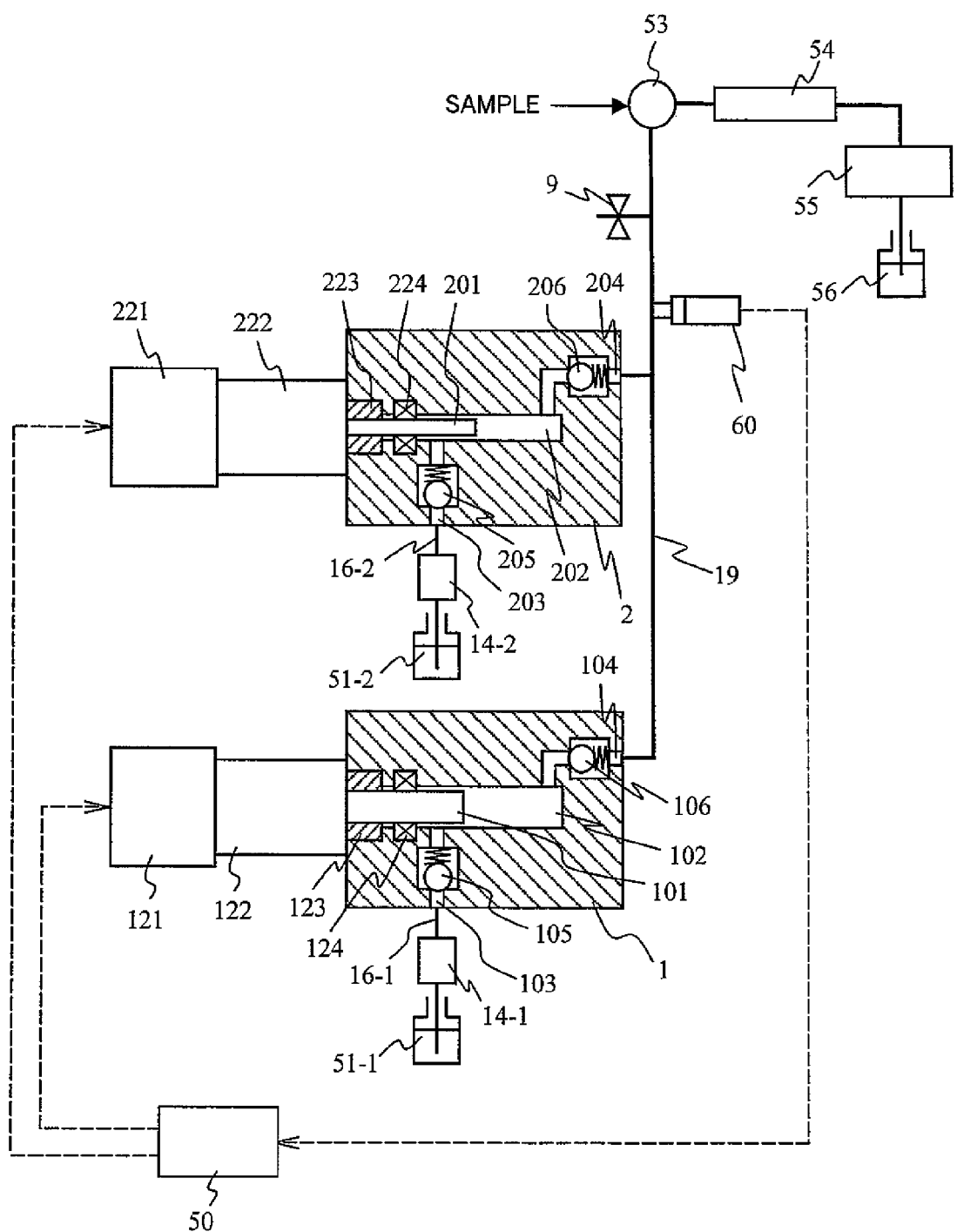
FIG. 13 is a block diagram for showing a still further preferred embodiment of the liquid feeding system of the present invention.

FIG. 13 shows another example of the liquid feeding system of the present invention. Same reference symbols are applied to the same portions in the liquid feeding system in FIG. 1 and their description will be properly eliminated. The feature of this example consists in the fact that the first pump and the second pump are constituted as separate pumps. The liquid feeding system in this example has two storing tanks 51-1, 51-2, two deaeration devices (de-gassing units) 14-1, 14-2, two plunger pump devices 1, 2, linear motion mechanisms (actuators) 122, 222, motors 121, 221 for driving the linear motion mechanisms and controller 50.

The two plunger pump devices 1, 2 are connected to the injector 53 through the discharging pipe 19. The discharging pipe 19 is provided with the drain valve 9 and the pressure sensor 60. Each of the two plunger pump devices 1, 2 corresponds to each of the first and second pumps. A flow rate of the first pump is larger than a flow rate of the second pump in the same manner as that of the first example.

Each of the first and second plunger pump devices 1, 2 has the first and second pressurizing chambers 102, 202 and these pressurizing chambers are liquid-tightly sealed with seals 124, 224. Each of the first and second plungers 101, 201 is arranged at each of the first and second pressurizing chambers 102, 202. The first and second plungers 101, 201 are slidably held by the bearings 123, 223.

A suction passage 103 and a discharging passage 104 are connected to the first pressurizing chamber 102. The suction passage 103 is connected to the storing tank 51-1 through the suction pipe 16-1 and the deaeration device 14-1. The suction passage 103 is provided with the suction check valve 105. The discharging passage 104 is connected to the discharging pipe 19. The discharging passage 104 is provided with the discharging check valve 106.

The suction passage 203 and the discharging passage 204 are connected to the second pressurizing chamber 202. The suction passage 203 is connected to the storing tank 51-2 through the suction pipe 16-2 and the deaeration device 14-2.

The suction pipe 203 is provided with the suction check valve 205. The discharging passage 204 is connected to the discharging pipe 19. The discharging passage 204 is provided with the discharging check valve 206.

Next, a pump operation in the liquid feeding system will be described. Under the air bubble discharging and eluate filling mode, the drain valve 9 is "opened", the two plunger devices are operated and air bubbles in each of the pressurizing chamber and the passage are discharged. Under the starting operation, the drain valve 9 is closed and only the first plunger 101 is operated. A flow rate of the first plunger 101 is larger than a flow rate of the second plunger 201. Accordingly, the pump discharging pressure easily reaches up to the target pressure. When the pump discharging pressure reaches up to the target pressure, the operation is changed from the starting operation to the normal operation. Under the normal operation, the drain valve 9 is closed, the first plunger pump device is stopped and only the second plunger device is operated. The second plunger is pushed into the second pressurizing chamber 202 at a slow speed. With such an operation as above, it is possible to accomplish the predetermined pump flow rate while holding the pump discharging pressure to the target pressure. In addition, although the discharging side of the pump in the preferred embodiment is provided with the discharging check valve, the aforesaid active valve may be applied.

The two pumps are separately arranged at the liquid feeding system in this example and both of them are connected by the pipe. Accordingly, a disassembling work for the pump becomes easy and maintenance work such a seal replacement work becomes easy. In addition, it can attain advantages that a layout characteristic of equipment is improved.

What is claimed is:

1. A liquid chromatograph device comprising:
    a first liquid feeding device for feeding a first solution,
    a second liquid feeding device for feeding a second solution, said first and second liquid feeding devices being connected to each other,
    a column which introduces said first and second solutions with sample and for separating a sample into its constituents, and
    a detector for analyzing the constituents,
    wherein said first and second solutions are fed through a discharge pipe to said column so that a mixing ratio between said first solution and said second solution is being changed in a stepwise manner as time passes by,
    said liquid chromatograph device further comprising a controller for giving a feed-back gain proportionate to a ratio between the two liquid feeding flow rates to a signal for controlling liquid feeding flow rates of said first and second liquid feeding devices.

2. The liquid chromatograph device according to claim 1 further comprising:
    a pressure sensor for detecting the discharge pressure to said discharge pipe,
    wherein said second liquid feeding device is started after said first liquid feeding device is started and said discharge pressure reaches a target pressure.

3. The liquid chromatograph device according to claim 1, wherein the flow rate of said first liquid feeding device is higher than that of said second liquid feeding device.

4. The liquid chromatograph device according to claim 1, each of said first and second liquid feeding devices comprising:
    a first and a second pumps each being driven by a motor, wherein an operating flow rate of said first pump is higher than an operating flow rate of said second pump.

5. The liquid chromatograph device according to claim 1, each of said first and second liquid feeding devices comprising:
    a first and a second pumps each being driven by a motor,
    a pressure sensor for detecting the discharge pressure of each of said first and second liquid feeding devices,
    wherein said second liquid feeding device is started after said first liquid feeding device is started and said the discharge pressure reaches a target pressure.

6. A liquid chromatograph device comprising:
    a first liquid feeding device for feeding a first solution,
    a second liquid feeding device for feeding a second solution,
    a first discharging pipe which is connected to said first liquid feeding device and for discharging said first solution from said first liquid feeding device,
    a second discharging pipe which is connected to said second liquid feeding device and for discharging said second solution from said second liquid feeding device,
    a connection for connecting between said first and second discharging pipes,
    an injector for pouring sample to be analyzed into the solution from said connection and for mixing said sampling with said solution, a column for introducing said solution from said injector and for separating said sample into its constituents,
    a detector for detecting said constituents from said column, and a controller for keeping a total flow rate of said first solution and said second solution at constant and for giving a feed-back gain proportionate to a ratio between the two liquid feeding flow rates.

7. The liquid chromatograph device according to claim 6 further comprising:
    a pressure sensor for detecting the discharge pressure to said first discharge pipe,
    wherein said second liquid feeding is started after said first liquid feeding device is started and said the discharge pressure detected by said pressure sensor reaches a predetermined pressure.

8. The liquid chromatograph device according to claim 7, wherein the flow rate of said first liquid feeding device is higher than that of said second liquid feeding device.

9. A liquid chromatograph device comprising:
    a first liquid feeding device for sucking a first solution from a first suction pipe and discharging said first solution to a first discharging pipe,
    a second liquid feeding device for sucking a second solution from a second suction pipe and discharging said second solution to said second solution to a second discharge pipe,
    a third discharge pipe by which said first and second discharge pipes are connected to each other,
    a column into which said first and second solutions are introduced with a sample and for separating the sample into its constituents, and
    a detector for analyzing the constituents,
    wherein said first and second solutions are fed through said third discharge pipe to said column so that a mixing ratio between said first solution and said second solution is being changed in a stepwise manner as time passes by,
    said first liquid feeding device including;
    a first pump and a second pump each being driven by a motor and positioned between said first suction pipe and said first discharge pipe,
    a first sensor for detecting a discharge pressure of said first solution discharged to said first discharge pipe, and
    a first active valve being movable between a first position for connecting said first suction pipe with said first pump and for shutting out said first pump from said second pump and a second position for shutting out said first suction pipe from said first pump and for connecting said first pump with said second pump, said second liquid feeding device including;
- a third pump and a fourth pump each being driven by a motor and positioned between said second suction pipe and said second discharge pipe,
- a second sensor for detecting a discharge pressure of said second solution discharged to said second discharge pipe, and
- a second active valve being movable between a first position for connecting said second suction pipe with said third pump and for shutting out said third pump from said fourth pump and a second position for shutting out said second suction pipe from said third pump and for connecting said third pump with said fourth pump, wherein said liquid chromatograph device further comprising a controller for giving a feed-back gain proportionate to a ratio between the two liquid feeding flow rates to a signal for controlling liquid feeding flow rates of said first and second liquid feeding devices in order to perform a gradient operation.

10. The liquid chromatograph device according to claim 9, wherein:

said first liquid feeding device is operated such that only said first pump is started with said second pump being stopped and said first active valve being positioned at said second position, and when said discharge pressure of said first solution reaches a target pressure, only said second pump is operated in a steady operation with said first active valve being positioned at said first position and said first pump being stopped, and said second liquid feeding device is operated such that only said third pump is started with said fourth pump being stopped and said second active valve being positioned at said second position, and when said discharge pressure of said second solution reaches a target pressure, only said fourth pump is operated in a steady operation with said second active valve being positioned at said first position and said third pump being stopped.

11. A liquid chromatograph device according to claim 9, further comprising a mixer for connecting said first discharge pipe with said second discharge pipe, wherein a discharge pressure of said mixer is detected and is compared with a pressure variation curve to obtain a deviation therebetween, and said first and second liquid feeding systems are driven with said deviation as a feed-back signal, said pressure variation curve indicating a relation between the mixing ratio and the pressure variation when the total liquid feeding flow rate is constant and being obtained from past experimental data.

* * * * *